US009593055B2

(12) United States Patent
Aliyev et al.

(10) Patent No.: US 9,593,055 B2
(45) Date of Patent: Mar. 14, 2017

(54) METHOD FOR PREPARING LINEAR ALPHA-OLEFINS

(75) Inventors: Vugar Aliyev, Riyadh (SA); Fuad Mosa, Riyadh (SA); Mohammed Al-Hazmi, Riyadh (SA); Syriac Palackal, Freising (DE); Ayed Al-Ayed, Riyadh (SA); Sultan Al-Otaibi, Riyadh (SA); Mohammed Zahoor, Riyadh (SA); Wolfgang Müller, Munich (DE); Peter M. Fritz, Unterhaching (DE); Heinz Bölt, Wolfratshausen (DE); Anton Wellenhofer, Munich (DE); Florian Winkler, Munich (DE); Uwe Rosenthal, Lambrechtshagen (DE); Hans-Jörg Zander, Munich (DE); Normen Peulecke, Wismar (DE); Bernd H. Müller, Rostock (DE); Karl-Heinz Hofmann, Germering (DE); Helmut Fritz, Munich (DE); Carsten Taube, Ebersberg (DE); Andreas Meiswinkel, Munich (DE); Richard Schneider, Uffing (DE); Anina Woehl, Pullach (DE)

(73) Assignees: SAUDI BASIC INDUSTRIES CORPORATION, Riyadh (SA); LINDE AG, Munich (DE)

( * ) Notice: Subject to any disclaimer, the term of this patent is extended or adjusted under 35 U.S.C. 154(b) by 682 days.

(21) Appl. No.: 12/735,585

(22) PCT Filed: Jan. 7, 2009

(86) PCT No.: PCT/EP2009/000030
§ 371 (c)(1),
(2), (4) Date: Nov. 2, 2010

(87) PCT Pub. No.: WO2009/095147
PCT Pub. Date: Aug. 6, 2009

(65) Prior Publication Data
US 2011/0046429 A1   Feb. 24, 2011

(30) Foreign Application Priority Data

Jan. 30, 2008   (EP) .................................... 08001377

(51) Int. Cl.
| C07C 2/02 | (2006.01) |
| C07C 2/04 | (2006.01) |
| C07C 2/08 | (2006.01) |
| C07C 2/30 | (2006.01) |

(52) U.S. Cl.
CPC .......... *C07C 2/30* (2013.01); *C07C 2531/025* (2013.01); *C07C 2531/04* (2013.01); *C07C 2531/14* (2013.01)

(58) Field of Classification Search
USPC ....... 585/502, 510, 511, 512, 520, 521, 522, 585/523
See application file for complete search history.

(56) References Cited

U.S. PATENT DOCUMENTS

| 3,862,257 | A | * | 1/1975 | Buben et al. ................. 585/523 |
| 4,486,615 | A | * | 12/1984 | Langer, Jr. ................... 585/523 |
| 4,713,424 | A | * | 12/1987 | Brown ...................... C07C 2/88 |
| | | | | 526/64 |
| 4,783,573 | A | | 11/1988 | Shiraki et al. |
| 5,811,619 | A | | 9/1998 | Commereuc et al. |
| 6,576,721 | B2 | * | 6/2003 | Kobayashi et al. ............ 526/70 |
| 2010/0217058 | A1 | | 8/2010 | Fritz et al. |
| 2011/0046429 | A1 | | 2/2011 | Aliyev et al. |

FOREIGN PATENT DOCUMENTS

| CA | 2036473 A1 | 2/1991 |
| CN | 1107828 A | 9/1995 |
| CN | 1197783 A | 11/1998 |
| EP | 0295690 A2 | 12/1988 |
| EP | 0444505 A2 | 9/1991 |
| EP | 1947075 A1 | 7/2008 |
| JP | 6341430 A | 2/1988 |
| JP | 3220135 A | 9/1991 |

(Continued)

OTHER PUBLICATIONS

Eller, et al., "Amines, Aliphatic" in Ullmann's Encyclopedia of Industrial Chemistry, Wiley-VCH, 2002, available on-line Jun. 15, 2000.*
Fabri, et al., "Xylenes" in Ullmann's Encyclopedia of Industrial Chemistry, Wiley-VCH, 2002, available on-line Jun. 15, 2000.*
Matthews, "Green Chemistry" in Kirk-Othmer Encyclopedia of Chemical Technology, John Wiley & Sons, 2001, available on-line Feb. 14, 2003.*
DE19807226A1; Oct. 15, 1998; Abstract Only; 2 pages.
DE433814C12; Mar. 16, 1995; Abstract Only; 1 page.
FR2857964A1; Jan. 28, 2005; Abstract Only; 1 page.
JP03-103406; Apr. 30, 1991; Abstract Only; 1 page.
International Search Report; International Application No. PCT/EP2009/000030; International Filing Date; Jan. 7, 2009; 3 pages, dated Mar. 3, 2009.

(Continued)

*Primary Examiner* — In Suk Bullock
*Assistant Examiner* — Youngsul Jeong
(74) *Attorney, Agent, or Firm* — Cantor Colburn LLP

(57) ABSTRACT

The present invention relates to a method for preparing linear alpha-olefins (LAO) by oligomerization of ethylene in the presence of solvent and homogenous catalyst, comprising the steps of: (i) feeding ethylene, solvent and catalyst into an oligomerization reactor, (ii) oligomerizing the ethylene in the reactor, (iii) removing a reactor outlet stream comprising solvent, linear alpha-olefins, ethylene, and catalyst from the reactor via a reactor outlet piping system, (iv) transferring the reactor outlet stream to a catalyst deactivation and removal step, and (v) deactivating and removing the catalyst from the reactor outlet stream, characterized in that at least one organic amine is added into the oligomerization reactor and/or into the reactor outlet piping system.

18 Claims, No Drawings

(56) References Cited

FOREIGN PATENT DOCUMENTS

| JP | 0853374 A | 2/1996 |
|----|-----------|--------|
| JP | 10218800 A | 8/1998 |
| KR | 100330938 | 9/2002 |
| WO | 0147839 A1 | 7/2001 |

OTHER PUBLICATIONS

Written Opinion; International Application No. PCT/EP2009/000030; International Filing Date; Jan. 7, 2009; 8 pages, dated Mar. 3, 2009.
International Search Report; International Application No. PCT/EP2010/003285; International Filing Date May 28, 2010; 3 pages, dated Oct. 29, 2010.
Written Opinion; International Application No. PCT/EP2010/003285; International Filing Date May 28, 2010; 8 pages, dated Oct. 29, 2010.
English Abstract of Japanese Patent No. 03220135A; Date of Publication Sep. 27, 1991; 2 pages.
English Abstract of Japanese Patent No. 10218800A; Date of Publication Aug. 18, 1998; 2 pages.
English Abstract of Chinese Patent No. 1107828A; Date of Publication Sep. 6, 1995; 1 page.
English Abstract of Japanese Patent No. 6341430A; Date of Publication Feb. 22, 1988; 2 pages.
Chinese Patent No. 1197783; Date of Publication: Nov. 4, 1998; Abstract Only, 1 page.
Extended European Search Report for Application No. 09009599.3; Date of Mailing: Dec. 10, 2009; 4 Pages.
Korean Patent Publication No. 10-0330938; Date of Publication: Sep. 4, 2002; Abstract Only, 2 pages.

* cited by examiner

METHOD FOR PREPARING LINEAR ALPHA-OLEFINS

The present invention relates to a method for preparing linear alpha-olefins (LAO).

Processes for the oligomerization of ethylene utilizing a homogenous catalyst are widely known. For example DE 43 38 414 C1 discloses a process for the oligomerization of ethylene to obtain linear alpha-olefins, wherein ethylene is catalytically converted in an empty tubular reactor utilizing a catalyst comprising a zirconium component and an aluminum component. The process is advantageously carried out in a continuous mode wherein gaseous and liquid outlet streams are obtained. The liquid outlet stream usually contains solvent, catalyst, dissolved ethylene and linear alpha-olefins. The catalyst may be preferably deactivated by caustic, although other quenching agents, such as water, alcohol or fatty acids, are known in the prior art. Preferably, the deactivated catalyst is also extracted from the phase containing solvent, ethylene and alpha-olefins.

One disadvantage of the prior art is that during the catalyst deactivation and catalyst removal step HCl is formed which may catalyse isomerization of LAO which is not desired. Due to the presence of HCl high, but limited purities of the desired LAO products are obtained only. Further, the sensitivity of the oligomerization for an unintended runaway reaction is quite high. Additionally, the LAO products obtained only have a limited thermal stability. Moreover, side reactions in the oligomerization reactor and in the reactor outlet piping system can take place, such as fouling, plugging by traces of high molecular weight linear alpha-olefins, which may have impact on product qualities. In the catalyst deactivation and removal step further a limited mixing efficiency of linear alpha-olefins and caustic can be present.

It is therefore an object of the present invention to provide a method for preparing linear alpha-olefins which overcomes the drawbacks of the prior art, especially to provide a method avoiding the formation of HCl during catalyst deactivation and to yield LAO products with high purity and thermal stability, wherein side reactions within the oligomerization reactor are substantially avoided.

The object is achieved by a method for preparing linear alpha-olefins (LAO) by oligomerization of ethylene in the presence of solvent and homogenous catalyst, comprising the steps of:

(i) feeding ethylene, solvent and catalyst into an oligomerization reactor,
(ii) oligomerizing the ethylene in the reactor,
(iii) removing a reactor outlet stream comprising solvent, linear alpha-olefins, ethylene, and catalyst from the reactor via a reactor outlet piping system,
(iv) transferring the reactor outlet stream to a catalyst deactivation and removal step, and
(v) deactivating and removing the catalyst from the reactor outlet stream, characterized in that at least one organic amine is added into the oligomerization reactor and/or into the reactor outlet piping system.

Preferably, the amine is mixed with catalyst components prior to feeding the catalyst components into the oligomerization reactor.

Preferably the amine is added continuously.

The organic amine may be a primary, secondary, tertiary or cyclic amine.

In one embodiment, the organic amine is soluble in an organic phase containing linear alpha-olefins.

It is further preferred that the organic amine is insoluble or has a low solubility in water or a mixture of water and caustic.

The organic amine may be preferably removed from the reactor outlet stream or one or more products by distillation, extraction or adsorption.

In a most preferred embodiment, the removed organic amine is recycled into the reactor and/or the reactor outlet piping system, preferably together with the solvent.

The added amine may be dissolved in a solvent, preferably toluene or a linear alpha olefin fraction or a linear alpha olefin product.

It is additionally convenient that the amine is mixed in the reactor outlet piping system with the reactor outlet stream by means of a mixing device, preferably a static mixer, a dynamic mixer, an ultrasonic mixer or a ventury mixing nozzle.

In a further embodiment the amine is mixed with catalyst components prior to charging catalyst and amine into the oligomerization reactor.

It is further preferred that the catalyst is deactivated by caustic.

In one embodiment, the amine has a boiling point differing from the boiling point of the solvent utilized of not more than 20° C., preferably not more than 10° C., preferably not more than 5° C.

It is preferred that the catalyst comprises a zirconium salt of organic acids and at least one organo aluminum compound.

Even preferred is that the zirconium salt has the formula $ZrCl_{4-m}X_m$, wherein X=$OCOR$ or $OSO_3R'$ with R and R' being independently alkyl, alkene or phenyl, and wherein $0<m<4$.

Also preferred is that the organic amine is added in an amount of 0.1 to 2.0 mol equivalent to chloride, preferably 0.5 to 1.0 mol equivalent to chloride.

It is further preferably proposed that the at least one aluminum compound has the general formula $R^1{}_nAl_{3-n}$ or $Al_2Y_3R^1{}_3$, wherein $R^1$ represents an alkyl group having from 1 to 20 carbon atoms, Y represents Cl, Br or I, n is any number within the range $1<n<2$.

Surprisingly it was found that by utilizing the inventive method, i.e. adding an organic amine into the oligomerization reactor and/or the reactor outlet piping system, the disadvantages of the prior art can be avoided.

In detail no formation of HCl during the catalyst deactivation and the removal step was observed. Additionally, increased purities of LAO products were obtained, since HCl is not present. Moreover, an improved reaction stability was achieved, i.e. less sensitivity to reaction runaway since amines act as moderator for the reaction. Since acid-catalyzed side reactions in the removal section are inhibited (no acidic sites are present), the LAO products additionally have increased thermal stability.

It was further recognized that dosing of an adequate amount of amine into the reactor outlet line completely prevents fouling and plugging of the reactor outlet piping system. Even more surprisingly, it has been found that partially fouled or plugged outlet lines could be deplugged by using adequate flow rates of amine dosing. Additionally, mixing of amine with catalyst components prior to feeding these catalyst components into the oligomerization reactor resulted in an increase of product purities and a reduced fouling/plugging within the oligomerization reactor.

It was further found that side reactions in the oligomerization reactor and reactor outlet piping system are suppressed.

Finally, the mixing efficiency in the mixing system of LAO and caustic within the catalyst deactivation and removal step is increased, probably due to the tenside effect of amines.

In a most preferred method, the organic amine is removed from the reactor outlet stream by distillation, extraction or adsorption and the removed organic amine is then recycled into the reactor and/or the reactor outlet piping system. Recycling can be preferably together with a solvent, but most preferably with a fraction of the LAO products, most preferably the C10-C12 fraction. Recovery and recycling of the dosed amine results in a significant improvement of the economics of the process, since the costs for the amine are reduced considerably. There are hardly any costs for an imported fresh amine, but only for a small make-up stream to cover any losses from the plant.

Preferably, organic amines are utilized which have a good solubility in the organic phase containing linear alpha-olefins, but have no or only a low solubility in water or a mixture of water and caustic. For example, amines which include acidic groups are not suitable, e.g. amino-acids, monoethyl amine (MEA), diethyl amine (DEA), etc.

Additional features and advantages ob the inventive method will now become apparent from the detailed description of a preferred embodiment thereof.

Ethylene is oligomerized in a suitable reactor, for example an empty tubular reactor as disclosed in DE 43 38 414 C1, utilizing a catalyst comprising a zirconium component and an aluminum component. A suitable zirconium component is zirconium tetraisobutyrate, and a suitable aluminum component is ethyl aluminum sesquichloride.

The oligomerization is carried out under conditions (temperature, pressure, etc.) known in the art. Ethylene, solvent and catalyst are introduced. From the reactor, a liquid organic outlet stream is discharged into a reactor outlet piping system containing solvent, for example toluene, catalyst, ethylene dissolved in the solvent, and linear alpha-olefins. This liquid organic outlet stream is transferred to a catalyst deactivation and removal section. The catalyst is deactivated by caustic and is removed from the outlet stream. The caustic phase may contain alkali metal hydroxide, preferably NaOH and/or KOH. The reactor comprises a feedline for feeding an organic amine into the oligomerization reactor and/or a feedline for feeding the organic amine into the reactor outlet piping system. The amine added can be mixed, e.g., with catalyst components outside of the oligomerization reactor and can then be fed mutually thereto. Additionally or alternatively, the amine added into the reactor outlet piping system can be mixed with the reactor outlet stream by means of a mixing device such as a static mixer, dynamic mixer, ultrasonic mixer or ventury mixing nozzle.

The amines can be routed through the separation unit of the LAO plant for separating the linear alpha-olefins into separate fractions, end up in one or more products and are removed from the products e.g. by distillation, extraction or adsorption.

In an other embodiment, the amine can be already removed from the reactor outlet stream prior to separation of the outlet stream into individual fractions, also by distillation, extraction or adsorption.

The amine may be utilized in a once-through operation mode.

Preferably, the amines are recovered by any means (e.g. by distillation or extraction) and can be recycled to the oligomerization reactor or the reactor outlet piping system.

In a more detailed example, a mixture of 3-ethyl-heptyl-amine and LAO's recycled from the separation section of an LAO plant is dosed into the LAO reactor outlet line. The dosing quantity is adjusted to achieve an amine concentration of 1000 wt ppm.

The amine, which has a boiling point between the C10 and C12 LAO products, is routed to the separation section of the LAO plant together with the total LAO fraction.

In the separation section, the amine is removed from the LAO products by conventional distillation. Remaining traces of the amine in the C10 and C12 products will be removed by adequate adsorbers, depending on the required product specification. The production of a pure amine fraction is not required, since the amine is recycled to the LAO reactors, i.e. the recycled stream is a mixture of 3-ethyl-heptyl-amine and C10 and C12 LAO's.

A small amine make-up stream from an amine storage vessel is fed into the amine system in order to compensate any amine losses. Thus, the separation section is provided to remove the amine from the LAO products, and, optionally, also already to provide a separation of the LAO product into separate fractions for further processing. Preferably, the separation section is after the catalyst deactivation and removal step.

The addition of an organic amine into a method for preparing linear alpha-olefines by the oligomerization of ethylene results in the advantages as already outlined above.

The features disclosed in the foregoing description and in the claims may, both separately and in any combination thereof, be material for realizing the invention in diverse forms thereof.

The invention claimed is:

1. A method for producing linear alpha-olefins (LAO) by an oligomerization of ethylene in the presence of a reaction feed comprising a solvent and a homogenous catalyst, comprising the steps of:
   (i) contacting ethylene with the reaction feed under oligomerization conditions and producing a reaction product, comprising, linear alpha-olefins, the solvent, ethylene, and the homogeneous catalyst;
   (ii) removing the reaction product as a reactor outlet stream via a reactor outlet piping system;
   (iii) transferring the reactor outlet stream to a catalyst deactivation and removal step;
   (iv) deactivating and removing the homogeneous catalyst from the reactor outlet stream, wherein at least one organic amine is added to the reaction feed and/or the reaction product prior to catalyst deactivation; and
   (v) recovering the organic amine from the reaction product after catalyst deactivation, wherein the organic amine is removed from the reactor outlet stream by distillation, extraction, or adsorption to obtain a recovered organic amine, and recycling the recovered organic amine to the reaction feed and/or the reaction product prior to catalyst deactivation.

2. The method according to claim 1, wherein the organic amine is soluble in an organic phase comprising linear alpha-olefins.

3. The method according to claim 1, wherein the organic amine is insoluble or has a low solubility in water.

4. The method according to claim 1, wherein the organic amine is insoluble or has low solubility in a mixture of water and caustic material.

5. The method according to any of claim 3, wherein the organic amine is dissolved in a solvent or a linear alpha olefin.

6. The method according to claim 3, wherein the homogeneous catalyst is deactivated by reacting it with caustic.

7. The method according to claim 4, wherein the homogeneous catalyst is deactivated by reacting it with caustic.

8. The method according to claim 2, wherein the organic amine has a boiling point which differs from the boiling point of the solvent by not more than 10° C.

9. The method according to claim 2, wherein the organic amine has a boiling point which differs from the boiling point of the solvent by not more than 5° C.

10. The method according to claim 1, wherein the homogeneous catalyst comprises a zirconium salt of an organic acid and an organo aluminum compound, and the zirconium salt has the formula $ZrCl_{4-m}X_m$, wherein X=OCOR or $OSO_3R'$ with R and R' being independently alkyl, alkene or phenyl, and 0<m<4, and wherein the organo aluminum compound has the general formula $R^1{}_n Al_{3-n}$ or $Al_2Y_3R^1{}_3$, wherein $R^1$ represents an alkyl group having from 1 to 20 carbon atoms, Y represents Cl, Br or I, and n is 1 or 2.

11. The method according to claim 10, wherein the organic amine is added in an amount of 0.5 to 1.0 mol equivalent to chloride when the homogeneous catalyst comprises Cl.

12. The method according to claim 1, wherein the organic amine comprises 3-ethyl-heptyl-amine.

13. The method according to claim 1, wherein the organic amine comprises 3-ethyl-heptyl-amine and said organic amine is recovered from the reaction product by distillation of a distillation product which comprises LAO.

14. The method according to claim 13, wherein the organic amine is added in an amount of 0.5 to 1.0 mol equivalent to chloride when the homogenous catalyst comprises Cl.

15. The method according to claim 14, wherein the homogeneous catalyst is deactivated by reacting it with material caustic.

16. The method according to claim 1, wherein the organic amine is a primary, secondary, tertiary, or cyclic amine.

17. The method according to claim 16, wherein the organic amine is added continuously.

18. The method according to claim 17, wherein the removed organic amine is added to the reaction feed and/or the reaction product prior to catalyst deactivation together with the solvent.

* * * * *